(12) United States Patent
Tachiya

(10) Patent No.: US 8,207,376 B2
(45) Date of Patent: Jun. 26, 2012

(54) METHOD FOR PRODUCING AMINO ACID PHOSPHATES

(75) Inventor: Naohisa Tachiya, Satte (JP)

(73) Assignee: Cosmo Oil Co., Ltd., Tokyo (JP)

( * ) Notice: Subject to any disclaimer, the term of this patent is extended or adjusted under 35 U.S.C. 154(b) by 678 days.

(21) Appl. No.: 12/065,547

(22) PCT Filed: Mar. 1, 2007

(86) PCT No.: PCT/JP2007/053962
§ 371 (c)(1),
(2), (4) Date: Mar. 3, 2008

(87) PCT Pub. No.: WO2007/119302
PCT Pub. Date: Oct. 25, 2007

(65) Prior Publication Data
US 2009/0281347 A1 Nov. 12, 2009

(30) Foreign Application Priority Data
Mar. 13, 2006 (JP) .................................. 2006-066967

(51) Int. Cl.
*C07C 205/00* (2006.01)
(52) U.S. Cl. ........................................ 562/553; 560/155
(58) Field of Classification Search ........................ None
See application file for complete search history.

(56) References Cited

U.S. PATENT DOCUMENTS
| | | | | |
|---|---|---|---|---|
| 4,602,039 | A * | 7/1986 | Cavazza | 514/561 |
| 2007/0203027 | A1 * | 8/2007 | Tachiya et al. | 504/194 |

FOREIGN PATENT DOCUMENTS
| | | |
|---|---|---|
| EP | 1 731 500 A1 | 12/2006 |
| JP | 48-92328 A | 11/1973 |
| JP | 60-158152 A | 8/1985 |
| JP | 62-111954 A | 5/1987 |
| JP | 02-76841 A | 3/1990 |
| JP | 06-172281 A | 6/1994 |
| JP | 07-188133 A | 7/1995 |
| JP | 09-316041 A | 12/1997 |
| JP | 2003-252840 A | 9/2003 |
| WO | 2005-100300 A1 | 10/2005 |

OTHER PUBLICATIONS

Chemical Abstracts; May 13, 1963; 10303g-h-10304a; vol. 58, No. 10; Published by the "American Chemical Society".
Office Action issued by the Korean Patent Office dated Jan. 19, 2011 in a counterpart application No. 10-2008-7004709.
Australian Office Action issued on Apr. 12, 2011 in the corresponding Australian Patent Application No. 2007237792.
European Search Report, dated Jul. 15, 2011, issued in corresponding European Application No. 07737632.5.
Japanese Office Action dated Aug. 23, 2011, issued in corresponding Japanese Application No. 2006-066967.
Australian Office Action dated Aug. 16, 2011, issued in corresponding Australia Application No. 2007237792.
Chinese Office Action dated Jun. 23, 2011, issued in corresponding Chinese Application No. 2007800009428.
Communication issued on Dec. 13, 2011 by the European Patent Office in the corresponding European Patent Application No. 07737632.5.
Israeli Office Action dated Oct. 10, 2011, as issued in counter Israeli Patent Application No. 189295.
Notification of Reason for Rejection issued Nov. 2, 2011 by the Japanese Patent Office in counterpart Japanese Patent Application No. 2006-066967.

* cited by examiner

*Primary Examiner* — Sudhakar Katakam
(74) *Attorney, Agent, or Firm* — Sughrue Mion, PLLC

(57) ABSTRACT

To provide a production method of phosphates of amino acids, typified by δ-aminolevulinic acid phosphate, or esters thereof.
A method for producing phosphates of an amino acid or an ester thereof, which comprises allowing an amino acid, an ester thereof or a salt thereof to coexist with phosphoric acids and a basic nitrogen-containing compound.

5 Claims, No Drawings

METHOD FOR PRODUCING AMINO ACID PHOSPHATES

TECHNICAL FIELD

This invention relates to a method for producing amino acid phosphates which are useful in the field of microorganisms and fermentation, animals and medical treatment, plants and the like.

BACKGROUND OF THE INVENTION

Amino acids which are used in various applications in the field of microorganisms and fermentation, animals and medical treatment, plants and the like are present sometimes as hydrochloride, hydrobromide, hydroiodide, sulfonate, sulfate, nitrate and the like salts, but it is known that characteristics of the amino acids vary and their flexibility varies depending on the kinds of salt.

For example, it is known that since δ-aminolevulinic acid hydrochloride (cf. Patent References 1 to 6 for its production method) contains hydrochloric acid, it causes corrosion of devices and generation of irritating odor due to hydrogen chloride vaporized during its production process and compounding and dispersing process. In addition, it is known that δ-aminolevulinic acid hydrochloride has a problem of being sensitive to high temperature heating sterilization because it has a property in that it is partially degraded at from 130 to 156° C. and completely degraded at 156° C. or more.

Patent Reference 1: JP-A-48-92328
Patent Reference 2: JP-A-62-111954
Patent Reference 3: JP-A-2-76841
Patent Reference 4: JP-A-6-172281
Patent Reference 5: JP-A-7-188133
Patent Reference 6: JP-A-9-316041

DISCLOSURE OF THE INVENTION

Problems that the Invention is to Solve

Contrary to this, the phosphoric acid salt of δ-aminolevulinic acid invented by the present inventors in JP-A-2006-182753 has low stimulative nature, is easy to handle because it does not generate a bad smell, has low stimulative nature against the skin and tongue, and its permeability through the skin and the like is also excellent.

Accordingly, production of phosphate or the like salt of amino acid is in demand, but it is produced in the above application by a method in which the kind of salt is changed using an ion exchange resin and is also produced in another application (JP-A-2007-015937) by a method in which the amino group is chemically modified by a protective group and then the kind of salt is changed. However, the former has a problem regarding the ion exchange resin treatment, concentration treatment and the like complicated operations, and the latter regarding miscellaneous agents to be used in the chemical reaction and a problem, accompanied thereby, of the purification and yield of the product of interest, so that more convenient method has been in demand.

Accordingly, the invention aims at providing a method for producing phosphates of an amino acid typified by δ-aminolevulinic acid or an ester thereof.

Means for Solving the Problems

Taking such actual circumstances into consideration, the present inventors have carried out intensive examinations and found as a result a method for obtaining phosphates of an amino acid or an ester thereof by allowing the material amino acid, an ester thereof or a salt thereof to coexist with phosphoric acids and a basic nitrogen-containing compound, thereby accomplishing the invention.

That is, the invention provides a method for producing phosphates of an amino acid or an ester thereof, which comprises allowing an amino acid, an ester thereof or a salt thereof to coexist with phosphoric acids and a basic nitrogen-containing compound.

Advantage of the Invention

The method of the invention for producing phosphates of an amino acid or an ester thereof (to be referred also to as amino acids hereinafter) is a markedly convenient method by which the phosphate of interest can be obtained by merely allowing the material amino acid, an ester thereof or a salt thereof to coexist with phosphoric acids and a basic nitrogen-containing compound.

BEST MODE FOR CARRYING OUT THE INVENTION

According to this specification, not only organic compounds having both of amino group and carboxyl group in the same molecule but also proline, hydroxyproline and the like imino acids in which hydrogen of the amino group is substituted with the side chain moiety in the molecule to form a cyclic structure are included in the amino acid.

As the amino acid to be used in the material of the production method of the invention, an α-amino acid, a β-amino acid, a γ-amino acid and a δ-amino acid are desirable, valine, leucine, isoleucine, threonine, methionine, phenylalanine, tryptophan, lysine, arginine, histidine, asparagine, aspartic acid, cysteine, tyrosine, glycine, alanine, serine, glutamine, glutamic acid, ornithine, citrulline, proline, oxyproline, β-alanine, γ-aminobutyric acid and δ-aminolevulinic acid are more desirable, and δ-aminolevulinic acid is particularly desirable.

Those in which these amino acids became ester forms can also be used in the material of the production method of the invention. In this case, as the hydrocarbon group of the ester residue, alkyl group, alkenyl group, aryl group and aralkyl group can be exemplified. Regarding the number of carbons of the hydrocarbon group, those having from 1 to 40 can be exemplified.

As the alkyl group, a straight chain, branched chain or cyclic alkyl group can be exemplified, and an alkyl group having from 1 to 40, more preferably from 1 to 18, particularly from 1 to 7, carbon atoms is desirable. As the alkenyl group, a straight chain, branched chain or cyclic alkenyl group can be exemplified, and an alkenyl group having from 2 to 40, more preferably from 2 to 18, carbon atoms is desirable. As the aralkyl group, those which are constituted from an aryl group having from 6 to 20 carbon atoms and an alkyl group having from 1 to 6 carbon atoms can be exemplified. In addition, an aryl group having from 6 to 20 carbon atoms can be exemplified as the aryl group.

These may have a substituent, and a group selected from hydroxy group, an alkoxy group, an acyloxy group, an alkoxycarbonyloxy group, an amino group, an aryl group, an oxo group, fluoro group, chloro group and nitro group can be exemplified as the substituent. In this case, an alkoxy group having from 1 to 18 carbon atoms, particularly an alkoxy group having from 1 to 7 carbon atoms is desirable as the alkoxy group. An alkanoyloxy group having from 1 to 18 carbon atoms, particularly an alkanoyloxy group having from 2 to 8 carbon atoms is desirable as the acyloxy group. A $C_{1-18}$ alkoxy-carbonyloxy group, particularly a $C_{1-7}$ alkoxy-carbonyloxy group is desirable as the alkoxycarbonyloxy group.

As the desirable alkyl group having from 1 to 18 carbon atoms among the hydrocarbon of ester residue, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group, 2-methylhexyl group, n-octyl group, isooctyl group, tert-octyl group, 2-ethylhexyl group, 3-methylheptyl group, n-nonyl group, isononyl group, 1-methyloctyl group, ethylheptyl group, n-decyl group, 1-methylnonyl group, n-undecyl group, 1,1-dimethylnonyl group, n-dodecyl group, n-tridecyl group, n-tetradecyl group, n-pentadecyl group, n-hexadecyl group, n-heptadecyl group, n-octadecyl group and the like can be cited.

As more desirable alkyl group having from 1 to 7 carbon atoms, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group and 2-methylhexyl group can be cited.

The number of fluoro when substituted by fluoro may be within the range of from 1 to 37 and the substituting position is not limited, but preferred is a group represented by —$(CH_2)_M(CF_2)_NR^5$ [M is from 0 to 6, N is an integer of from 1 to 7, with the proviso that the total of M and N is from 1 to 7, and $R^5$ represents hydrogen or fluoro], and its examples include 2,2,2-trifluoroethyl, 3,3,3-trifluoropropyl, 2,2,3,3,3-pentafluoropropyl, 4,4,4-trifluorobutyl, 3,3,4,4,4-pentafluorobutyl, 2,2,3,3,4,4,4-heptafluorobutyl, 5,5,5-trifluoropentyl, 4,4,5,5,5-pentafluoropentyl, 2,2,3,3,4,4,5,5-octafluoropentyl, 3,3,4,4,5,5-hexafluoropentyl, 3,3,4,4,5,5,5-heptafluoropentyl, 2,2,3,3,4,4,5,5,5-nonafluoropentyl, 6,6,6-trifluorohexyl, 5,5,6,6,6-pentafluorohexyl, 4,4,5,5,6,6,6-heptafluorohexyl, 3,3,4,4,5,5,6,6,6-nonafluorohexyl, 2,2,3,3,4,4,5,5,6,6,6-undecafluorohexyl, 7,7,7-trifluoroheptyl, 6,6,7,7,7-pentafluoroheptyl, 5,5,6,6,7,7,7-heptafluoroheptyl, 4,4,5,5,6,6,7,7,7-nonafluoroheptyl, 3,3,4,4,5,5,6,6,7,7,7-undecafluoroheptyl, 2,2,3,3,4,4,5,5,6,6,7,7,7-tridecafluoroheptyl and the like, of which 2,2,3,3,4,4,4-heptafluorobutyl, 2,2,3,3,4,4,5,5-octafluoropentyl, 3,3,4,4,5,5,6,6,6-nonafluorohexyl and 2,2,3,3,4,4,5,5,6,6,7,7,7-tridecafluoroheptyl are particularly preferred.

As the alkyl group having from 1 to 18 carbon atoms in which hydroxy is substituted, 2-hydroxyethyl, 3-hydroxypropyl, 4-hydroxybutyl, 5-hydroxypentyl, 6-hydroxyhexyl and the like can be exemplified.

As the alkyl group having from 1 to 18 carbon atoms in which alkoxy is substituted, a $C_{1-7}$ alkoxy-$C_{1-18}$ alkyl group such as 2-methoxyethyl, 2-ethoxyethyl, 3-methoxypropyl, 3-ethoxypropyl, 4-methoxybutyl, 4-ethoxybutyl, 2-(2-methoxyethoxy)ethyl and the like can be exemplified.

As the alkyl group in which acyloxy group is substituted, a $C_{2-7}$ alkanoyloxy-$C_{1-18}$ alkyl group can be exemplified. As the alkyl group in which alkoxycarbonyloxy group is substituted, a $C_{1-18}$ alkoxy-carbonyloxy-$C_{1-18}$ alkyl group can be exemplified. As the alkyl group in which amino group is substituted, an amino-$C_{1-18}$ alkyl group can be exemplified.

As the alkenyl group having from 2 to 18 carbon atoms, vinyl group, allyl group, isopropenyl group, 2-butenyl group, 2-methylallyl group, 1,1-dimethylallyl group, 3-methyl-2-butenyl group, 3-methyl-3-butenyl group, 4-pentenyl group, hexenyl group, octenyl group, nonenyl group, decenyl group, cyclopropenyl group, cyclobutenyl group, cyclopentenyl group, cyclohexenyl group, cycloheptenyl group, cyclooctenyl group, 4-methylcyclohexenyl group, 4-ethylcyclohexenyl group, 2-cyclopentenylethyl group, cyclohexenylmethyl group, cycloheptenylmethyl group, 2-cyclobutenylethyl group, 2-cyclooctenylethyl group, 3-(4-methylcyclohexenyl) propyl group, 4-cyclopropenylbutyl group, 5-(4-ethylcyclohexenyl)pentyl group, oleyl group, vaccenyl group, linoleyl group, linolenyl group, trans-9-octadecenyl group, 9E, 12E-octadecadienyl group, 9E, 12E, 15E-octadecatrienyl group and the like can be exemplified.

As the aralkyl group having from 7 to 26 carbon atoms, those which are constituted from an alkyl group having from 1 to 6 carbon atoms and an aryl group having from to 20 carbon atoms are desirable. As the alkyl group having from 1 to 6 carbon atoms, for example, methyl group, ethyl group, n-propyl group, isopropyl group, n-butyl group, isobutyl group, tert-butyl group, n-pentyl group, n-hexyl group, cyclopropyl group, cyclobutyl group, cyclohexyl group and the like can be cited, and as the aryl group having from 6 to 20 carbon atoms, phenyl group, naphthyl group and the like can be cited. Among the aralkyl groups having from 7 to 26 carbon atoms, benzyl group, phenethyl group and 9-fluorenylmethyl group are desirable and benzyl group and phenethyl group are particularly desirable. The aryl group of the aralkyl group may be substituted by 1 to 3 substituent groups such as the aforementioned alkyl groups having from 1 to 6 carbon atoms, methoxy group, ethoxy group, n-propoxy group, n-butoxy group, isobutoxy group, tert-butoxy group and the like alkoxy groups having from 1 to 6 carbon atoms, hydroxyl group, amino group, nitro group, cyano group, fluorine, chlorine, bromine, iodine and the like halogen atoms, carboxy group and the like. As such a substituted aralkyl group, groups represented by —$CH_2C_6H_{4-p}F_pR^6$ ($R^6$ represents a group selected from hydrogen, fluoro, chloro, methyl, ethyl, propyl, butyl, trifluoromethyl, nitro and methoxy, and p is an integer of from 0 to 4) can be exemplified, of which 2-methylbenzyl, 3-methylbenzyl, 4-methylbenzyl, 4-methoxybenzyl, 4-trifluoromethylbenzyl, 4-chlorobenzyl, 3,4-dichlorobenzyl, 2-fluorobenzyl, 3-fluorobenzyl, 4-fluorobenzyl, 3-nitrobenzyl, 4-nitrobenzyl, 2,3,4,5-tetrafluorobenzyl and 2,3,4,5,6-pentafluorobenzyl are particularly desirable.

As the aryl group having from 6 to 20 carbon atoms, phenyl group, naphthyl group and the like can be exemplified, which may be substituted by 1 to 3 substituent groups such as methyl group, ethyl group, n-propyl group, isopropyl group, n-butyl group, isobutyl group, tert-butyl group, n-pentyl group, n-hexyl group, cyclopropyl group, cyclobutyl group, cyclohexyl group and the like alkyl groups having from 1 to 6 carbon atoms, methoxy group, ethoxy group, n-propoxy group, n-butoxy group, isobutoxy group, tert-butoxy group and the like alkoxy groups having from 1 to 6 carbon atoms, hydroxyl group, amino group, nitro group, cyano group, fluorine, chlorine, bromine, iodine and the like halogen atoms, carboxy group and the like.

A compound represented by the following formula (1)

$$R^1OCOCH_2CH_2COCH_2NH_2 \qquad (1)$$

(in the formula, $R^1$ represents a hydrogen atom or a hydrocarbon group having from 1 to 40 carbon atoms which may have a substituent) is desirable as the amino acid or an ester thereof to be used as the material of the production method of the invention. In this case, as the hydrocarbon group having from 1 to 40 carbon atoms which may have a substituent, those which were exemplified in the above as the hydrocarbon group of ester residue can be cited.

In addition, the amino acid or an ester thereof to be used as the material may be a salt. As the salt, for example, hydrochloride, hydrobromide, hydriodide, sulfonate, sulfate, nitrate, borate, carbonate, benzoate, phthalate, fumarate, gluceptate, citrate, succinate, acetate, lactate, tartarate, oxalate, maleate, edetate, gluconate, glycolate, hydroxynaphthoate, isethionate, malate, mandelate, pantothenate, salicylate, stearate, tannate and the like can be cited. Preferably, hydrochloride, hydrobromide, hydriodide, sulfonate, sulfate, nitrate and the like can be cited, of which hydrochloride is particularly preferable.

In this connection, the amino acid to be used in the production method of the invention may have either L type or D type structure.

Phosphoric acids represented by the following formula (2)

$$HOP(O)(OR^2)_b(OH)_{2-n} \quad (2)$$

(in the formula, $R^2$ represents a hydrogen atom or a hydrocarbon group having from 1 to 26 carbon atoms which may have a substituent, and n is an integer of 0 to 2) are desirable as the phosphoric acids to be used as a material of the production method of the invention.

As the hydrocarbon group having from 1 to 26 carbon atoms of $R^2$ in the formula (2), an alkyl group having from 1 to 18 carbon atoms, an alkenyl group having from 2 to 18 carbon atoms, an aralkyl group having from 7 to 26 carbon atoms or an aryl group having from 6 to 14 carbon atoms can be exemplified.

The alkyl group having from 1 to 18 carbon atoms represented by $R^2$ may be any one of straight chain, branched chain and cyclic chain. As the straight chain or branched chain alkyl group, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group, 2-methylhexyl group, n-octyl group, isooctyl group, tert-octyl group, 2-ethylhexyl group, 3-methylheptyl group, n-nonyl group, isononyl group, 1-methyloctyl group, ethylheptyl group, n-decyl group, 1-methylnonyl group, n-undecyl group, 1,1-dimethylnonyl group, n-dodecyl group, n-tridecyl group, n-tetradecyl group, n-pentadecyl group, n-hexadecyl group, n-heptadecyl group, n-octadecyl group and the like can be cited.

As the cyclic chain or alkyl group containing a cyclic chain, for example, cyclopropyl group, cyclobutyl group, cyclopentyl group, cyclohexyl group, cycloheptyl group, cyclooctyl group, 2-cyclopropylethyl group, 2-cyclobutylethyl group, 2-cyclopentylethyl group, cyclohexylmethyl group, 2-cyclohexylethyl group, cycloheptylmethyl group, 2-cyclooctylethyl group, 3-methylcyclohexyl group, 4-methylcyclohexyl group, 4-ethylcyclohexyl group, 2-methylcyclooctyl group, 3-(3-methylcyclohexyl)propyl group, 2-(4-methylcyclohexyl)ethyl group, 2-(4-ethylcyclohexyl)ethyl group, 2-(2-methylcyclooctyl)ethyl group and the like can be cited. As the aforementioned alkyl group having from 1 to 18 carbon atoms, an alkyl group having from 1 to 16 carbon atoms is desirable and methyl group, ethyl group, n-butyl group, n-hexadecyl group or 2-ethylhexyl group is particularly desirable.

As the alkenyl group having from 2 to 18 carbon atoms, vinyl group, allyl group, isopropenyl group, 2-butenyl group, 2-methylallyl group, 1,1-dimethylallyl group, 3-methyl-2-butenyl group, 3-methyl-3-butenyl group, 4-pentenyl group, hexenyl group, octenyl group, nonenyl group, decenyl group, cyclopropenyl group, cyclobutenyl group, cyclopentenyl group, cyclohexenyl group, cycloheptenyl group, cyclooctenyl group, 4-methylcyclohexenyl group, 4-ethylcyclohexenyl group, 2-cyclopentenylethyl group, cyclohexenylmethyl group, cycloheptenylmethyl group, 2-cyclobutenylethyl group, 2-cyclooctenylethyl group, 3-(4-methylcyclohexenyl) propyl group, 4-cyclopropenylbutyl group, 5-(4-ethylcyclohexenyl)pentyl group, oleyl group, vaccenyl group, linoleyl group, linolenyl group and the like can be exemplified, and oleyl group is desirable.

As the aralkyl group having from 7 to 26 carbon atoms, those which are constituted from an alkyl group having from 1 to 6 carbon atoms and an aryl group having from 6 to 20 carbon atoms are desirable. As the alkyl group having from 1 to 6 carbon atoms, for example, methyl group, ethyl group, n-propyl group, isopropyl group, n-butyl group, isobutyl group, tert-butyl group, n-pentyl group, n-hexyl group, cyclopropyl group, cyclobutyl group, cyclohexyl group and the like can be cited, and as the aryl group having from 6 to 20 carbon atoms, phenyl group, naphthyl group and the like can be cited. Among the aralkyl groups having from 7 to 26 carbon atoms, benzyl group or phenethyl group is desirable and benzyl group is particularly desirable. The aryl group of the aralkyl group may be substituted by 1 to 3 substituent groups such as the aforementioned alkyl groups having from 1 to 6 carbon atoms, methoxy group, ethoxy group, n-propoxy group, n-butoxy group, isobutoxy group, tert-butoxy group and the like alkoxy groups having from 1 to 6 carbon atoms, hydroxyl group, amino group, nitro group, cyano group, fluorine, chlorine, bromine, iodine and the like halogen atoms, carboxy group and the like.

As the aryl group having from 6 to 14 carbon atoms, for example, phenyl group, naphthyl group, anthryl group, phenanthryl group and the like can be exemplified and phenyl group is desirable.

As the substituent which may be possessed by the hydrocarbon of these $R^2$, a group selected from hydroxy group, an alkoxy group, an acyloxy group, an alkoxycarbonyloxy group, an amino group, an aryl group, an oxo group, fluoro group, chloro group and nitro group can be exemplified. In this case, an alkoxy group having from 1 to 18 carbon atoms, particularly an alkoxy group having from 1 to 7 carbon atoms is desirable as the alkoxy group. An alkanoyloxy group having from 1 to 18 carbon atoms, particularly an alkanoyloxy group having from 2 to 8 carbon atoms is desirable as the acyloxy group. As the alkoxycarbonyloxy group, a $C_{1-18}$ alkoxy-carbonyloxy group, particularly a $C_{1-7}$ alkoxy-carbonyloxy group, is desirable.

As these $R^2$, hydrogen atom, methyl group, ethyl group, n-butyl group, hexadecyl group, 2-ethylhexyl group, oleyl group, benzyl group or phenyl group is desirable.

Though the basic nitrogen-containing compound to be used in the production method of the invention is not particularly limited, pyridines and amines can be exemplified of which amines are desirable.

As the pyridines to be used, a compound represented by the following formula (3)

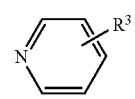

(3)

(in the formula, $R^3$ represents a hydrogen atom, a hydrocarbon group having from 1 to 40 carbon atoms which may have a substituent or amino group which may have a substituent group) is desirable.

In this case, an alkyl group and an aralkyl group can be exemplified as the hydrocarbon group. In this case, a straight chain, branched chain or cyclic alkyl group can be exemplified as the alkyl group, and an alkyl group having from 1 to 40, further from 1 to 18, particularly from 1 to 7, carbon atoms is desirable. In addition, an aryl group having from 6 to 20 carbon atoms can be exemplified as the aryl group.

As the desirable alkyl group having from 1 to 18 carbon atoms, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group, 2-methylhexyl group, n-octyl group, isooctyl group, tert-octyl group, 2-ethylhexyl group, 3-methylheptyl group, n-nonyl group, isononyl group, 1-methyloctyl group, ethylheptyl group, n-decyl group, 1-methylnonyl group, n-undecyl group, 1,1-dimethylnonyl group, n-dodecyl group, n-tridecyl group, n-tetradecyl group, n-pentadecyl group, n-hexadecyl group, n-heptadecyl group, n-octadecyl group and the like can be cited.

As the more desirable alkyl group having from 1 to 7 carbon atoms, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group and 2-methylhexyl group can be exemplified.

As the aryl group having from 6 to 14 carbon atoms, for example, phenyl group, naphthyl group, anthryl group, phenanthryl group and the like can be exemplified of which phenyl group is desirable.

As the substituent which may be possessed by the hydrocarbon of these $R^3$, a group selected from hydroxy group, an alkoxy group, an acyloxy group, an alkoxycarbonyloxy group, an amino group, an aryl group, an oxo group, fluoro group, chloro group and nitro group can be exemplified. In this case, an alkoxy group having from 1 to 18 carbon atoms, particularly an alkoxy group having from 1 to 7 carbon atoms is desirable as the alkoxy group. An alkanoyloxy group having from 1 to 18 carbon atoms, particularly an alkanoyloxy group having from 2 to 8 carbon atoms is desirable as the acyloxy group. As the alkoxycarbonyloxy group, a $C_{1-18}$ alkoxy-carbonyloxy group, particularly a $C_{1-7}$ alkoxy-carbonyloxy group, is desirable.

As the substituent in the amino group which may have a substituent, an alkyl group having from 1 to 18 carbon atoms, an aryl group having from 6 to 16 carbon atoms and an aralkyl group having from 7 to 20 carbon atoms can be exemplified, of which an alkyl group having from 1 to 6 carbon atoms is more desirable and methyl group, ethyl group and propyl group are particularly desirable.

As desirable pyridines, pyridine, α-picoline, β-picoline, γ-picoline and 4-dimethylaminopyridine can be exemplified.

In addition, as the amines to be used, amines represented by the following formula (4):

$$NH_m R^4{}_{3-m} \qquad (4)$$

(in the formula, m is an integer of from 0 to 3, and $R^4$ represents a hydrogen atom or a hydrocarbon group having from 1 to 40 carbon atoms which may have a substituent) are desirable.

In this case, an alkyl group, an aryl group and an aralkyl group can be exemplified as the hydrocarbon group.

A straight chain, branched chain or cyclic alkyl group can be exemplified as the alkyl group, and an alkyl group having from 1 to 40, further from 1 to 18, particularly from 1 to 7, carbon atoms is desirable. Those which are constituted from an aryl group having from 6 to 20 carbon atoms and an alkyl group having from 1 to 6 carbon atoms can be exemplified as the aralkyl group. In addition, an aryl group having from 6 to 20 carbon atoms can be exemplified as the aryl group.

As the desirable alkyl group having from 1 to 18 carbon atoms, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group, 2-methylhexyl group, n-octyl group, isooctyl group, tert-octyl group, 2-ethylhexyl group, 3-methylheptyl group, n-nonyl group, isononyl group, 1-methyloctyl group, ethylheptyl group, n-decyl group, 1-methylnonyl group, n-undecyl group, 1,1-dimethylnonyl group, n-dodecyl group, n-tridecyl group, n-tetradecyl group, n-pentadecyl group, n-hexadecyl group, n-heptadecyl group, n-octadecyl group and the like can be cited.

As the more desirable alkyl group having from 1 to carbon atoms, for example, methyl group, ethyl group, n-propyl group, isopropyl group, n-butyl group, isobutyl group, tert-butyl group, n-pentyl group, isopentyl group, neopentyl group, tert-pentyl group, 2-methylbutyl group, n-hexyl group, isohexyl group, 3-methylpentyl group, ethylbutyl group, n-heptyl group and 2-methylhexyl group can be exemplified.

As these alkyl groups, methyl group, ethyl group, n-propyl group, isopropyl group, n-butyl group, isobutyl group, tert-butyl group, n-pentyl group and isopentyl group are desirable.

As the aralkyl group having from 7 to 26 carbon atoms, those which are constituted from an alkyl group having from 1 to 6 carbon atoms and an aryl group having from to 20 carbon atoms are desirable. As the alkyl group having from 1 to 6 carbon atoms, for example, methyl group, ethyl group, n-propyl group, isopropyl group, n-butyl group, isobutyl group, tert-butyl group, n-pentyl group, n-hexyl group, cyclopropyl group, cyclobutyl group, cyclohexyl group and the like can be cited, and as the aryl group having from 6 to 20 carbon atoms, phenyl group, naphthyl group and the like can be cited. Among the aralkyl groups having from 7 to 26 carbon atoms, benzyl group, phenethyl group and 9-fluorenylmethyl group are desirable and benzyl group and phenethyl group are particularly desirable.

As the aryl group having from 6 to 20 carbon atoms, phenyl group, naphthyl group and the like can be exemplified of which phenyl group is desirable.

As the substituent which may be possessed by the hydrocarbon of these $R^4$, a group selected from hydroxy group, an alkoxy group, an acyloxy group, an alkoxycarbonyloxy group, an amino group, an aryl group, an oxo group, fluoro group, chloro group and nitro group can be exemplified. In this case, an alkoxy group having from 1 to 18 carbon atoms, particularly an alkoxy group having from 1 to 7 carbon atoms is desirable as the alkoxy group. An alkanoyloxy group having from 1 to 18 carbon atoms, particularly an alkanoyloxy group having from 2 to 8 carbon atoms is desirable as the acyloxy group. As the alkoxycarbonyloxy group, a $C_{1-18}$ alkoxy-carbonyloxy group, particularly a $C_{1-7}$ alkoxy-carbonyloxy group, is desirable.

As desirable amines, for example, ammonia, methylamine, dimethylamine, trimethylamine, ethylamine, diethylamine, triethylamine, n-propylamine, di-n-propylamine, tri-n-propylamine, isopropylamine, diisopropylamine, triisopropylamine, n-butylamine, di-n-butylamine, tri-n-butylamine and aniline can be cited, of which triethylamine is desirable.

According to the invention, the phosphates of amino acids of interest are produced by allowing the material amino acid, an ester thereof or a salt thereof to coexist with phosphoric acids and a basic nitrogen-containing compound.

As an example of the production method of the invention, the phosphates of amino acids of interest can be produced by dissolving or suspending the material amino acid, an ester thereof or a salt thereof and the phosphoric acids desired to effect salt formation in a solvent and adding a basic nitrogen-containing compound thereto while stirring. The solvent is not particularly limited with the proviso that it is a hydrophilic solvent, but is preferably water or an alcohol, more preferably water, methanol, ethanol, n-propanol or isopropanol.

The reaction temperature is not particularly limited, with the proviso that freezing of the solvent and evaporation of the contents to dryness do not occur, but is preferably from 0° C. to 30° C. because heat is frequently generated when the basic nitrogen-containing compound is allowed to undergo the reaction.

The reaction time can be optionally selected in response to the solvent and reaction temperature but is generally from 1 minute to 24 hours and preferably from minutes to 2 hours.

Using amount of the phosphates of the reaction material is not particularly limited with the proviso that it is 1 mole or more based on the material amino acids, but is generally from 1 mole to 20 moles, preferably from mole to 5 moles, based on the material amino acids.

Using amount of the basic nitrogen-containing compound as a reaction material is not particularly limited. When amines which are not forming a salt are used as a reaction material, desirable using amount of the basic nitrogen-containing compound is generally from 0.01 mole to 20 moles, particularly preferably from 0.1 mole to 5 moles, based on the material amino acids. On the other hand, when amines which are forming a salt are used as a reaction material, desirable blending amount of the basic nitrogen-containing compound is generally from 0.1 mole to 50 moles, particularly preferably from 1 mole to 5 moles, based on the material amino acids.

After completion of the reaction, the reaction product can be precipitated by adding a solvent which has a lower solubility for the reaction product in comparison with the reaction solvent. Amount of the adding solvent having lower solubility can be optionally adjusted in response to its kind and kind and amount of the reaction solvent.

The thus precipitated reaction product can be recovered by filtration or the like generally used solid-recovering method.

In addition, when amino acids which formed a salt are used as a reaction material during the reaction, an acid which originally formed a salt with an amino acid sometimes reacts with the added basic nitrogen-containing compound to form an impurity salt and thereby generates precipitation, but it does not exert particular influence upon the reaction. In this connection, after completion of the reaction, the reaction product can be precipitated by adding a solvent which has a lower solubility for the reaction product, and the impurity salt is generally dissolved at that time though it depends on the kind and amount of the solvent used in the reaction and the kind and amount of the solvent used in the precipitation.

Regarding the reaction solvent/recovery solvent combination suited for forming the aforementioned reaction-precipitation, water/methanol, water/ethanol, water/isopropanol, methanol/ethanol and methanol/isopropanol can be cited as an example.

EXAMPLES

The following describes the invention further in detail with reference to examples, but the invention is not limited thereto.

Example 1

Synthesis of L(+)-lysine phosphate (Synthesis of α-amino acid phosphate)

A 25 g (137 mmol) portion of L(+)-lysine hydrochloride and 19.14 g (166 mmol) of 85% phosphoric acid were dissolved in 200 ml of purified water, and 15.21 g (150.50 mmol) of triethylamine was added dropwise thereto while stirring for 10 minutes on an ice bath. After completion of the dropwise addition and subsequent stirring at room temperature for 20 minutes, 500 ml of ethanol was added thereto and stirred. The thus precipitated precipitate was recovered by suction filtration, washed with 300 ml of ethanol and then dried at room temperature for 15 hours under a reduced pressure. A 32.43 g (133 mmol) portion of L(+)-lysine phosphate was obtained at a yield of 97 mol %.

$^1$H-NMR (D$_2$O, 400 MHz) δ ppm: 1.48 (2H, CH$_2$), 1.73 (2H, CH$_2$), (2H, CH$_2$), 3.02 (2H, CH$_2$), 3.76 (1H, CH)

$^{13}$C-NMR (D$_2$O, 100 MHz) δ ppm: 24 (CH$_2$), 29 (CH$_2$), 33 (CH$_2$) 42 (CH$_2$), 57 (CH), 178 (COO)

The ion content of the thus obtained L(+)-lysine phosphate was measured by an ion chromatography. The measured results are shown in Table 1.

TABLE 1

|  | Measured value | Theoretical value |
| --- | --- | --- |
| PO$_4^{3-}$ | 39% | 38.90% |
| Cl$^-$ | 0.4% | 0% |

Ion chromatography analytical conditions; separation column: IonPac AS12A manufactured by Nihon Dionex Co., Ltd., eluting solution: an aqueous solution containing Na$_2$CO$_3$ and NaHCO$_3$ (Na$_2$CO$_3$: 3.0 mmol/l, NaHCO$_3$: 0.5 mmol/l), flow rate: 1.5 ml/min., sample injection: 25 μl, column temperature: 35° C., detector: electric conductivity detector.

Example 2

Synthesis of δ-aminolevulinic acid phosphate

A 40 g (239 mmol) portion of δ-aminolevulinic acid hydrochloride and 18 ml (263 mmol) of 85% phosphoric acid were dissolved in 120 ml of purified water, and 25.4 g mmol) of triethylamine was added dropwise thereto while stirring on an ice bath. After completion of the dropwise addition and subsequent stirring at room temperature for 10 minutes, 1.6 L of ethanol was added thereto and stirred. The thus precipitated precipitate was recovered by suction filtration and dried at room temperature for 16 hours under a reduced pressure. A 51 g (224 mmol) portion of δ-aminolevulinic acid phosphate was obtained at a yield of 93 mol %.

Melting Point: 108-109° C.

$^1$H-NMR (D$_2$O, 400 MHz) δ ppm: 2.67 (t, 2H, CH$_2$), 2.86 (t, 2H, CH$_2$), 4.08 (s, 2H, CH$_2$)

$^{13}$C-NMR (D$_2$O, 100 MHz) δ ppm: 30 (CH$_2$), 37 (CH$_2$), 50 (CH$_2$) 180 (CO), 207 (COO)

The PO₄³⁻ content by an ion chromatography:
Theoretical value: 41.45%
Measured value: 43%
Ion chromatography analytical conditions; separation column: IonPac AS12A manufactured by Nihon Dionex Co., Ltd., eluting solution: an aqueous solution containing Na₂CO₃ and NaHCO₃ (Na₂CO₃: 3.0 mmol/l, NaHCO₃: 0.5 mmol/l), flow rate: 1.5 ml/min., sample injection: 25 μl, column temperature: 35° C., detector: electric conductivity detector.

Example 3

Synthesis of δ-aminolevulinic acid methyl ester phosphate

A 30 g (165 mmol) portion of δ-aminolevulinic acid methyl ester hydrochloride and 20.9 g (181 mmol) of 85% phosphoric acid were dissolved in 30 ml of purified water, and 17.5 g (173 mmol) of triethylamine was added dropwise thereto while stirring on an ice bath. After completion of the dropwise addition and subsequent stirring at room temperature for 10 minutes, 400 ml of ethanol was added thereto and stirred. The thus precipitated precipitate was recovered by suction filtration and dried at room temperature for 17 hours under a reduced pressure. A 37 g (154 mmol) portion of δ-aminolevulinic acid methyl ester phosphate was obtained at a yield of 93 mol %.
¹H-NMR (D₂O, 400 MHz) δ ppm: 2.68 (2H, CH₂), 2.89 (2H, CH₂) 3.66 (3H, CH₂), 4.10 (2H, CH₂)
¹³C-NMR (D₂O, 100 MHz) δ ppm: 30 (CH₂), 37 (CH₂), 50 (CH₂) 55 (CH₃), 178 (CO), 207 (COO)
The PO₄³⁻ content by an ion chromatography:
Theoretical value: 39.4%
Measured value: 40%
Ion chromatography analytical conditions; separation column: IonPac AS12A manufactured by Nihon Dionex Co., Ltd., eluting solution: an aqueous solution containing Na₂CO₃ and NaHCO₃ (Na₂CO₃: 3.0 mmol/l, NaHCO₃: 0.5 mmol/l), flow rate: 1.5 ml/min., sample injection: 25 μl, column temperature: 35° C., detector: electric conductivity detector.

Example 4

Synthesis of δ-aminolevulinic acid benzyl ester phosphate

A 8 g (31 mmol) portion of δ-aminolevulinic acid benzyl ester hydrochloride and 4 g (34.7 mmol) of 85% phosphoric acid were dissolved in 8 ml of purified water, and 3.3 g (32.7 mmol) of triethylamine was added dropwise thereto while stirring on an ice bath. After completion of the dropwise addition and subsequent stirring at room temperature for 10 minutes, 300 ml of ethanol was added thereto and stirred. The thus precipitated precipitate was recovered by suction filtration and dried at room temperature for 16 hours under a reduced pressure. An 8.5 g (27 mmol) portion of δ-aminolevulinic acid benzyl ester phosphate was obtained at a yield of 87 mol %.
¹H-NMR (D₂O, 400 MHz) δ ppm: 2.72 (2H, CH₂), 2.89 (2H, CH₂), 4.07 (2H, CH₂), 5.13 (2H, CH₂), 7.40 (5H, phenyl)
¹³C-NMR (D₂O, 100 MHz) δ ppm: 30 (CH₂), 37 (CH₂), 50 (CH₂), 70 (CH₂), 131.2 (phenyl), 131.6 (phenyl), 131.7 (phenyl), 138 (phenyl), 177 (CO), 207 (COO)

Example 5

Synthesis of δ-aminolevulinic acid phosphate

A 10.05 g (60.6 mmol) portion of δ-aminolevulinic acid hydrochloride and 4.5 ml (65.7 mmol) of 85% phosphoric acid were dissolved in 30 ml of purified water, and 5.83 g (62.7 mmol) of γ-picoline was added dropwise thereto while stirring. After completion of the dropwise addition and subsequent stirring at room temperature for 10 minutes, 400 ml of ethanol was added thereto and stirred. The thus precipitated precipitate was recovered by suction filtration and dried at room temperature for 19 hours under a reduced pressure. A 10.55 g (46.1 mmol) portion of δ-aminolevulinic acid phosphate was obtained at a yield of 77 mol %.

While the invention has been described in detail and with reference to specific embodiments thereof, it will be apparent to one skilled in the art that various changes and modifications can be made therein without departing from the spirit and scope of the invention.

This application is based on a Japanese patent application filed on Mar. 13, 2006 (Japanese Patent Application No. 2006-66967), the entire contents thereof being thereby incorporated by reference.

INDUSTRIAL APPLICABILITY

According to the invention, a production method of phosphates of amino acids, typified by δ-aminolevulinic acid phosphate, or esters thereof can be provided.

The invention claimed is:
1. A method for producing phosphates of an amino acid or an ester thereof, which comprises allowing a salt of an amino acid or a salt of an amino acid ester to mix and react with phosphoric acids and a basic nitrogen-containing compound in a hydrophilic solvent, wherein an amount of the basic nitrogen-containing compound is from 0.1 mole to 5 moles based on the salt of an amino acid or the salt of an amino acid ester; and
wherein the basic nitrogen-containing compound is pyridines represented by the following formula (3):

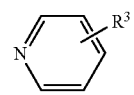

(3)

(in the formula, R³ represents a hydrogen atom, a hydrocarbon group having from 1 to 40 carbon atoms which may have a substituent or amino group which may have a substituent), or amines represented by the following formula (4):

NH_mR⁴_{3-m}   (4)

(in the formula, m is an integer of from 0 to 2, and R⁴ represents a hydrocarbon group having from 1 to 18 carbon atoms which may have a substituent).
2. The method according to claim 1, wherein the amino acid is selected from α-amino acids, β-amino acids, γ-amino acids and δ-amino acids.
3. The method according to claim 1 or 2, wherein the salt of an amino acid or the salt of an amino acid ester is a salt of a compound represented by the following formula (1):

R¹OCOCH₂CH₂COCH₂NH₂   (1)

(in the formula, $R^1$ represents a hydrogen atom or a hydrocarbon group having from 1 to 40 carbon atoms which may have a substituent).

4. The method according to claim 3, wherein the phosphoric acids are phosphoric acids represented by the following formula (2):

$$HOP(O)(OR^2)_n(OH)_{2-n} \qquad (2)$$

(in the formula, $R^2$ represents a hydrogen atom or a hydrocarbon group having from 1 to 26 carbon atoms which may have a substituent, and n is an integer of 0 to 2).

5. The method according to claim 1, wherein the salt of an amino acid or the salt of an amino acid ester is first mixed with phosphoric acids, and then the basic nitrogen-containing compound is added to the resulting mixture.

* * * * *